(12) United States Patent
Muschler (10) Patent No.: US 6,723,131 B2
(45) Date of Patent: Apr. 20, 2004

(54) COMPOSITE BONE MARROW GRAFT MATERIAL WITH METHOD AND KIT

(75) Inventor: George F. Muschler, Cleveland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 217 days.

(21) Appl. No.: 09/795,254

(22) Filed: Feb. 28, 2001

(65) Prior Publication Data

US 2002/0161449 A1 Oct. 31, 2002

(51) Int. Cl.$^7$ .................................................. A61F 2/36
(52) U.S. Cl. ................................. 623/23.51; 623/23.58
(58) Field of Search ........................... 623/23.61, 23.51, 623/23.56, 23.62, 23.63, 23.75

(56) References Cited

U.S. PATENT DOCUMENTS

| | | |
|---|---|---|
| 4,608,199 A | 8/1986 | Caplan et al. |
| 4,609,551 A | 9/1986 | Caplan et al. |
| 5,197,985 A | 3/1993 | Caplan et al. |
| 5,226,914 A | 7/1993 | Caplan et al. |
| 5,433,330 A * | 7/1995 | Yatsko et al. ............... 215/247 |
| 5,486,359 A | 1/1996 | Caplan et al. |
| 5,569,308 A * | 10/1996 | Sottosanti ................... 424/422 |
| 5,626,861 A | 5/1997 | Laurencin et al. |
| 5,645,729 A | 7/1997 | Priegnitz et al. |
| 5,700,289 A | 12/1997 | Breitbart et al. |
| 5,718,899 A | 2/1998 | Gristina et al. |
| 5,733,542 A | 3/1998 | Haynesworth et al. |
| 5,766,618 A | 6/1998 | Laurencin et al. |
| 5,824,084 A * | 10/1998 | Muschler ..................... 128/898 |
| 5,914,121 A | 6/1999 | Robey et al. |
| 6,037,519 A | 3/2000 | McKay |
| 6,045,555 A | 4/2000 | Smith et al. |
| 6,049,026 A | 4/2000 | Muschler |
| 6,142,998 A | 11/2000 | Smith et al. |

FOREIGN PATENT DOCUMENTS

WO 97/40137 10/1997

* cited by examiner

*Primary Examiner*—Corrine McDermott
*Assistant Examiner*—Hieu Phan
(74) *Attorney, Agent, or Firm*—Pearne & Gordon LLP

(57) ABSTRACT

A composite bone marrow graft material is provided having an enriched population of uniformly distributed progenitor cells. The graft material includes clot material preferably derived from non-anticoagulated bone marrow aspirate, which significantly improves the efficacy of the graft. A method for preparing such bone graft material is also provided. A kit is also provided containing sterilized implements useful in preparing enriched composite bone marrow graft material.

36 Claims, 3 Drawing Sheets

FIG. 8

COMPOSITE BONE MARROW GRAFT MATERIAL WITH METHOD AND KIT

BACKGROUND OF THE INVENTION

Bone grafting is widely used to treat fractures, non-unions and to induce arthrodeses. Autogenous cancellous bone, which is taken from one site in the graftee and implanted in another site in the graftee, is currently the most effective bone graft. Autogenous cancellous bone provides the scaffolding to support the distribution of the bone healing response, and progenitor cells which form new cartilage or bone. However, harvesting autogenous bone results in significant cost and morbidity, including scars, blood loss, pain, prolonged operative and rehabilitation time and risk of infection. Furthermore, the volume of the graft site can exceed the volume of available autograft.

Accordingly, alternatives to autografts have been developed. Several purified or synthetic materials, including ceramics, biopolymers, processed allograft bone and collagen-based matrices have been investigated or developed to serve as substitutes for autografts. The FDA has approved a porous coral-derived synthetic hydroxyapatite ceramic for use in contained bone defects. A purified collagen/ceramic composite material is also approved for use in acute long bone fractures. Although these materials avoid the morbidity involved in harvesting autografts and eliminate problems associated with a limited amount of available autograft, the clinical effectiveness of the synthetic materials remains generally inferior to autografts. The synthetic graft materials have also been used as carriers for bone marrow cells. When the above composite materials are implanted into skeletal defects, progenitor cells differentiate into skeletal tissue.

In some instances, composite implants are made by combining a synthetic graft material in a cell suspension with a similar or lesser volume obtained from a bone marrow aspirate. However, the progenitor cells, which have the capacity to differentiate into cartilage, bone, muscle, fibrous tissue, and other connective tissue, are present in the bone marrow in very miniscule amounts. The numbers of progenitor cells present in 1 ml of bone marrow varies widely between patients from about 100 cells to 20,000 cells. This represents a mean of about one in 20,000 to one in 40,000 of the nucleated cells in a bone marrow aspirate. Thus, a composite implant made by combining a given volume of synthetic graft material in a comparable volume of fresh bone marrow contains relatively few progenitor cells.

Accordingly, a technique has been previously developed to increase the relative concentration of progenitor cells in composite implants. This technique involves plating a suspension of bone marrow cells onto tissue culture dishes, culturing the cells in a select medium for one or more days to achieve an enhanced population of progenitor cells, and then detaching the cells from the tissue culture dishes to provide a cell suspension containing an increased population of progenitor cells. Composite implants are then made by soaking synthetic ceramic carriers in this progenitor cell enriched suspension. Unfortunately, this method of preparing composite implants is very time consuming. Moreover, if the original progenitor culture cells are derived from bone marrow aspirates obtained from the graftee, the graftee must undergo multiple invasive procedures; one procedure to remove his or her bone marrow, and another procedure on a later date to implant the composite graft. Consequently, the graftee may be exposed to anesthesia more than once.

Another technique has also been developed to produce a composite bone graft matrix having the benefits of the culture method, but is not so time consuming and does not require multiple invasive procedures. In this technique, a composite matrix having an enriched population of progenitor cells is produced by contacting a particular volume of matrix material with an excess volume of bone marrow aspirate (see U.S. Pat. Nos. 5,824,084 and 6,049,026). In that technique, bone marrow aspirate containing progenitor cells is passed through a porous matrix material having a surface which selectively bonds to progenitor cells, thus retaining the progenitor cells within the matrix and allowing excesses of other cells (such as blood cells and other nucleated marrow-derived cells) to pass through. The now progenitor cell-enriched graft matrix is implanted in a patient.

However, because progenitor cells are so strongly and selectively bonded to some matrix surfaces (e.g. allograft bone matrix), they are nonuniformly distributed throughout the matrix, with dense pockets of progenitor cells discretely concentrated in the vicinity of initial contact between the marrow aspirate and the matrix material. Consequently, a bone graft prepared by this technique suffers from the limitation that bone healing subsequent to implantation does not occur uniformly due to the nonuniform distribution of progenitor cells within the implanted matrix. Additionally, bone healing subsequent to implantation of the matrix occurs relatively slowly.

It is therefore desirable to have a new method of preparing composite bone marrow graft material having an enriched population of progenitor cells which can be performed intraoperatively, i.e. at the same time bone marrow is being taken from the graftee, that results in uniform distribution of progenitor cells throughout the graft material, and that facilitates accelerated healing upon implantation.

SUMMARY OF THE INVENTION

A composite bone marrow graft material is provided comprising a porous biocompatible implantable matrix and clot material. The composite bone marrow graft material has an enriched population of progenitor cells. A method of preparing composite bone marrow graft material is also provided. The method includes the steps of providing a bone marrow aspirate, providing a porous biocompatible implantable matrix, contacting the bone marrow aspirate and the matrix to provide an enriched matrix, and mechanically mixing the enriched matrix to yield a composite bone marrow graft material having progenitor cells distributed substantially uniformly throughout the composite bone marrow graft material.

A kit for the preparation of composite bone marrow graft material is also provided. The kit includes a matrix container, a first endcap, and a first loading syringe. The first loading syringe is adapted to mate to the first endcap to provide fluid communication between the first loading syringe and the matrix container. The first endcap is releasably attachable to the matrix container.

DETAILED DESCRIPTION OF THE PREFERRED EMBODIMENTS OF THE INVENTION

As used herein, when a range such as 5–25 or between 5 and 25 is given, this means preferably at least 5 and, separately and independently, preferably not more than 25. As used herein, the term "progenitor cell" or "progenitor cells" means any progenitor cells, such as connective tissue progenitor cells and/or stem cells. This population of cells contains cells that are pleuripotent and capable of differentiating into a variety of tissues (e.g. bone, cartilage, fat, tendon, ligament, muscle, nervous tissue, hematopoetic tissues, endothelial and vascular tissues, and liver).

A method of providing composite bone marrow graft material having an enriched population of progenitor cells according to the present invention generally comprises the following steps: 1. obtaining a bone marrow aspirate; 2. contacting the bone marrow aspirate with a porous biocompatible implantable matrix (e.g. by flowing the aspirate through the matrix) to provide a progenitor cell-enriched matrix having an enriched population of progenitor cells; 3. mechanically mixing the enriched matrix to provide substantially uniform progenitor cell distribution throughout; and 4. draining the matrix of excess liquid. Preferably, the method also includes the step of adding clot material to the enriched matrix. Composite bone marrow graft material thus prepared is then implantable into a patient or graftee, and is effective to induce bone healing and/or bone regeneration.

The steps of a method as outlined above comprise several functional elements which will now be described. Such functional elements include a bone marrow aspirate, a porous biocompatible implantable matrix, and preferably clot material. Following a description of these functional elements is a description of the preferred methods and apparatus for preparing a composite bone graft of the present invention. It should be understood that the descriptions that follow are by way of illustration only, and not limitation.

Bone Marrow Aspirate

Bone marrow aspirate contains plasma, nucleated progenitor cells (progenitor cells), nucleated hematopoietic cells, endothelial cells, and cells derived from peripheral blood, including red cells and platelets. Because bone marrow aspirate contains peripheral blood, it is preferred that the aspirate be collected in a syringe containing an anticoagulant. Suitable anticoagulants include heparin, sodium citrate, and EDTA. Preferably, a bone marrow aspirate for use in a method of the present invention is obtained from the patient who will receive the graft (the graftee). Less preferably, the bone marrow aspirate can be obtained from another immunologically compatible donor.

Porous Biocompatible Implantable Matrix

The matrix comprises a porous, biocompatible, implantable matrix. Preferably, the matrix has a bioactive surface. Examples of porous biocompatible, implantable graft matrix materials having a bioactive surface include ceramics comprising calcium phosphate such as hydroxyapatite or tricalcium phosphate, as well as demineralized or mineralized bone matrix. Other suitable matrix materials include biopolymers such as polylactic acid, polyglycolic acid, polygalactic acid, polycaprolactone, polyethylene oxide, polypropylene oxide, polysulfone, polyethylene, and polypropylene. Still other suitable matrix materials are hyaluronic acid, which may be purified with or without crosslinking, bioglass and collagen.

More preferably, cell adhesion molecules are bound to the surface of the matrix substrate. The term "cell adhesion molecules" includes laminins, fibronectin, vitronectin, vascular cell adhesion molecules (V-CAM), intercellular adhesion molecules (I-CAM), tenascin, thrombospondin, osteonectin, osteopontin, bone sialoprotein, collagens, or any other molecules or components effective to promote selective adhesion of progenitor cells to the substrate surface.

Preferably, the matrix has sufficient porosity to yield at least a 2-fold, preferably 3-fold, preferably 5-fold, preferably 7-fold, preferably 10-fold, increase in total matrix surface area available for progenitor cell-adhesion relative to a nonporous solid having identical external dimensions. Such an increase in total surface area can be achieved by using a matrix substrate comprising powder, granules, fibers, some combination thereof, or a single highly porous substrate mass. Preferably, the size of the pores in the matrix is greater that 20, more preferably 50, more preferably 100, more preferably 500, most preferably 1000 $\mu$m, in order to facilitate penetration of progenitor cells through the pore openings into the void volume of the matrix material, thereby availing of the additional surface area within the pores.

Particularly suitable matrix materials include isolated mineralized cancellous bone sections, powders or granules of mineralized bone, demineralized cancellous bone sections, powders or granules of demineralized bone, guanidine-HCl extracted demineralized bone matrix, sintered cortical or cancellous bone, coralline hydroxyapatite sold by Interpore under the trade name Interpore 500, or Interpore 200, granular ceramics such as that incorporated into the bone graft substitute Collagraft sold by Zimmer, granular or block ceramics such as that incorporated into the graft substitute Vitoss sold by Orthovita, and filamentous sponges such as those made from collagen by Orquest.

A preferred matrix is prepared as a combination of particulate bone material and fibrous bone material. The particulate bone material is preferably derived from spongy human bone, preferably cancellous bone, for example, from a distal end of long human bones. The fibrous bone material is preferably derived from cortical bone. Both the particulate and the fibrous bone materials can be obtained from a bone bank, or optionally from the graftee. When obtained from the graftee, the bone material is manipulated intraoperatively in the operating room to conform to the desired particulate and fibrous characteristics via known bone manipulation means.

Most preferably, the particulate bone material is provided as allograft cancellous bone particles in the form of chunks, chips or fragments, having dimensions in the range of 1–15, preferably 2–8, mm in mean diameter. Most preferably, the fibrous bone material is provided as allograft demineralized cortical bone fibers of at least 5 mm, more preferably at least 1 cm, more preferably at least 2 cm, more preferably at least 3 cm, more preferably at least 4 cm, and most preferably at least 5 cm, in length. Optionally the fibrous bone material is provided as a mixture of fibers of varying lengths in the range of 5 mm–2 cm, 5 mm–3 cm, 5 mm–4 cm, 5 mm–5 cm, 5mm–15 cm, or some other range. Optionally, the fibrous bone material is supplied as a flexible mat, e.g. Grafton Flex available from Osteotech, Inc.

The particulate and fibrous bone materials are combined to form a preferred composite matrix in the following manner. Bone fibers, preferably demineralized cortical bone fibers having lengths as described above, are combined with particulate bone particles in the following preferred proportion: about 225, less preferably 200–300, less preferably 150–375, less preferably 100–450, less preferably 75–500, less preferably 25–1000, mg dry weight of demineralized cortical bone fibers, with about 10, less preferably 8–12, less preferably 6–14, less preferably 4–16, less preferably 2–18, less preferably 1–25, cc (bulk volume) of particulate bone particles having a mean diameter of 1–15, preferably 2–8, mm. Optionally, demineralized cortical bone fibers can be obtained from a flexible mat comprising such fibers. When such a mat is used, it is first washed free of any toxic or hyperosmolar material that may be present, such as glycerol, using an isotonic solution. The mat is then suspended in saline, or other suitable isotonic solution, to facilitate separation of the individual bone fibers. The separated bone fibers are combined with particulate bone material in the following proportion to form a preferred composite matrix: the fibers from one mat having initial dimensions of 2.5 cm×5 cm×about 2.5 mm (initial volume of about 3.1 cm$^3$) with about 10 cc, less preferably 8–12 cc, less preferably 6–14 cc, less preferably 4–16 cc, (bulk volume) of particulate bone particles having a mean diameter of 1–15, preferably 2–8, mm.

It should be noted that when grafts of differing size are necessary, a composite matrix of different size can be prepared to conform with the above-stated proportion of fibrous to particulate bone according to the present invention. For example, (assuming uniform bulk density) 20 cc of particulate bone can be combined with 450 mg of bone fibers to provide a preferred composite matrix.

Clot Material

The clot material can be a blood clot formed from blood obtained from a vein or artery of the graftee (or an immunologically compatible donor). More preferably, the clot material is a bone marrow clot formed from non-anticoagulated bone marrow aspirate which is most preferably obtained from the graftee. Preferably, the bone marrow aspirate from which the bone marrow clot is formed is obtained from the graftee intraoperatively during the graft procedure. Less preferably, the clot material can be platelet gel, platelet concentrate, fibrin clot material, and/or fibrin glue as known in the art.

Addition of a bone marrow clot (obtained from non-anticoagulated bone marrow aspirate) to a progenitor cell-enriched graft matrix surprisingly significantly improves the efficacy of the resulting composite bone marrow graft material relative to composite grafts without clot material. It has been observed that addition of a marrow clot to a similarly enriched matrix delivering 50–70% more nucleated cells (including more than twice the number of progenitor cells) compared to a marrow clot alone resulted in a graft that was superior to both an enriched matrix alone and to a non-enriched matrix combined with a marrow clot. Hence, the addition of a bone marrow clot to a progenitor cell-enriched matrix provides improved graft performance.

Without wishing to be bound by any particular theory, it is believed that inclusion of a bone marrow clot may improve the efficacy of a composite bone graft for one or several of the following reasons. First, it is possible that some cells important to the process of successful bone healing do not attach to the graft matrix and therefore are not sufficiently concentrated in (or possibly are even excluded from) the graft site, resulting in ineffective or inefficient healing at that site. The polymerization of fibrinogen into fibrin resulting from the clotting cascade (further explained below) may provide a valuable supplemental matrix promoting the attachment and migration of cells important to the healing response at the graft site. Such cells include migratory endothelial cells which proliferate to form tubular structures that are important precursors to the formation of blood vessels via angiogenesis.

A second possibility is that the physiologic process of forming a clot at the graft site creates an improved environment for transplanted osteogenic cells at that site. Specifically, clotting of the non-anticoagulated bone marrow aspirate results in the activation of platelets contained therein, resulting in platelet degranulation. Platelet degranulation in turn releases growth factors and osteotropic cytokines which might otherwise be absent from the graft site. Several important bioactive factors released during this process include platelet derived growth factor (PDGF), epidermal growth factor (EGF), fibroblast growth factors (FGFs), and transforming growth factor beta (TGF-beta) In addition, fibrin matrix formed from fibrinogen as a result of the clotting cascade may provide important stability at the graft site during the immediate post-operative period. Furthermore, the process of fibrinolytic activity that occurs over the first several days following graft implantation provides an additional source for angiogenic factors (e.g. fibrin split products as known in the art) during the early stages of graft incorporation. It is believed that the resulting angiogenesis at the graft site following implantation may enhance the formation of new blood vessels in the site providing a source of nourishment for the freshly implanted progenitor cells and other cells responsible for bone healing and growth, thus accelerating the healing response.

Preferred Embodiments and Apparatus

Figure 1:
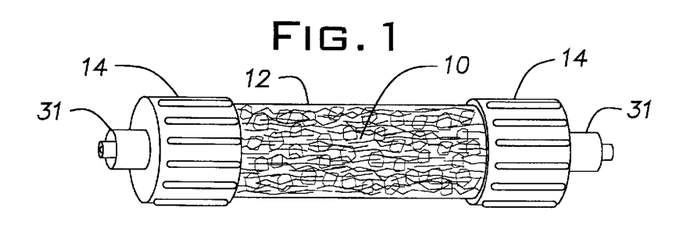
FIG. 1 is a perspective view of a matrix container fitted with endcaps and containing a graft matrix.

The preferred embodiments of the invented method for providing a composite bone graft will now be described. The apparatus parts described herein are preferably made from plastic, preferably transparent or translucent. According to a first preferred embodiment of the invention, and referring first to FIG. 1, a composite biocompatible implantable matrix 10 prepared as described above is placed into a matrix container, which container is most preferably a column 12. (Matrix 10 may be packed tightly or loosely, depending on the material and its structure) Column 12 can be provided having a multitude of interior volumes suitable to accommodate the necessary volume of matrix for a particular graft. As used herein, a volume of matrix (or matrix volume) refers to the excluded volume of a nonporous solid having external dimensions identical to those of the particular matrix. For example, a column having an internal volume of 5, 10, 15, 20, 25, or 30, cc, or some other internal volume, can be provided to accommodate various matrix volumes. Preferably, column 12 has an interior diameter of 0.5–3.0, more preferably 1–2, more preferably 1–1.5 cm. Preferably, column 12 has a length at least 1.5, more preferably at least 2, most preferably at least 3, times greater than its interior diameter. Endcaps 14 are removably attached to column 12 via threaded connections, snap connections, or any other known connecting means.

Optionally, endcaps 14 can be provided with a screen or membrane 15 (see FIG. 8) effective to allow aspirate 20 to pass therethrough, while retaining particles of matrix 10. Preferably, such a membrane has openings of at least 20, preferably at least 30, preferably at least 40, μm in diameter.

Figure 2:
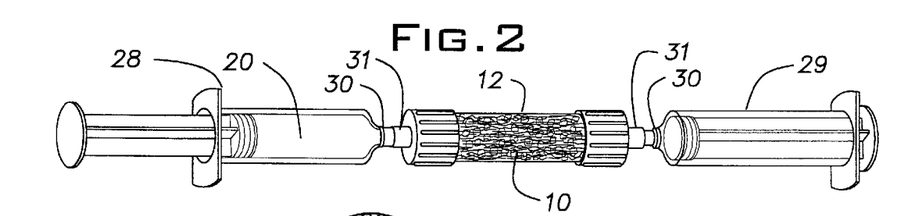
FIG. 2 is a perspective view of the matrix container of FIG. 1 fitted with loading syringes.

A bone marrow aspirate 20 (preferably containing an anticoagulant) is obtained via known means, preferably from the graftee. Aspirate 20 is then loaded into a first loading syringe 28. Initially, aspirate 20 contains progenitor cells 32 and other nucleated cells 33 in a ratio between 1:20,000 and 1:40,000 (see FIG. 2A). The aspirate also contains platelets, red blood cells and serum (including molecules which are soluble or suspended in serum). Loading syringe 28 is provided with a syringe connector 30 adapted to mate with endcap connector 31, to provide fluid communication between the respective interior volumes of loading syringe 28 and column 12. A second loading syringe 29 is similarly provided with a syringe connector 30 adapted to mate with endcap connector 31. As seen in FIG. 2 first and second loading syringes 28 and 29 are then attached at opposite ends of column 12 to endcaps 14 via the above-described connectors, thus providing fluid communication between the interior volumes of first loading syringe 28, column 12, and second loading syringe 29.

First loading syringe 28 is then plunged, delivering aspirate 20 into column 12 where aspirate 20 flows through or contacts matrix 10 prior to being collected at the opposite end of column 12 in second loading syringe 29. Contacting the bone marrow aspirate and the matrix to provide an enriched matrix can be done by flowing the aspirate through the matrix, incubating the matrix in the aspirate, or by other means known in the art. Alternatively, aspirate 20 is contacted with matrix 10 by any known means to provide an enriched matrix. Progenitor cells advantageously and selectively adhere to the surface of matrix 10, and hence are retained within the matrix while excesses of other cells, such as blood cells and other marrow-derived nucleated cells, flow relatively freely through the matrix and are collected in second loading syringe 29. To achieve an enriched progenitor cell population in matrix 10, the volume of aspirate 20 flowed through matrix 10 preferably exceeds the matrix volume. In this manner, the progenitor cells present in the aspirate volume are preferably concentrated in the matrix volume, providing an enriched matrix. As used herein, "enriched" means that the ratio of progenitor cells to all nucleated bone marrow cells is greater in the matrix than in the original bone marrow aspirate. Preferably the ratio of progenitor cells to all marrow-derived nucleated cells in an enriched matrix is at least 1:20,000, more preferably at least 1:10,000, more preferably at least 1:5,000, representing at least a 2-fold, preferably at least a 4-fold increase in progenitor cell prevalence or concentration. More preferably, an enriched matrix comprises at least a 5-fold, more preferably at least a 6-fold, more preferably at least an 8-fold, increase in progenitor cell concentration in the enriched matrix above that of a non-enriched matrix with a marrow clot. Preferably, the ratio of aspirate volume to matrix volume is at least 2:1, more preferably at least 3:1, more preferably at least 4:1. For example, when a matrix having a matrix volume of 15 cc is used, the total volume of aspirate passed through the matrix is preferably at least 30 cc, more preferably at least 45 cc, more preferably at lest 60 cc. Optionally, the initial effluent from column 12 delivered to second loading syringe 29 can be discarded prior to continuing the method.

Optionally, aspirate 20 is caused to flow back and forth through matrix 10 in column 12 by alternately plunging first and second loading syringes 28 and 29. Depending upon the rate of binding of cells and progenitors to a particular matrix, this procedure of flowing aspirate 20 through matrix 10 is repeated at least 1 time, but may be repeated preferably at least 2, preferably at least 3, preferably at least 4, times. Optionally, a wash solution is passed through matrix 10 after the original bone marrow aspirate suspension and any effluents have been passed through matrix 10. Preferably, the wash solution comprises a sterile, isotonic, buffered solution having a pH range of 7.3 to 7.5. Suitable wash solutions include, phosphate-buffered saline, Hank's balanced salt solution, human serum, and minimal essential medium.

Figures 2A, 3, 3A:
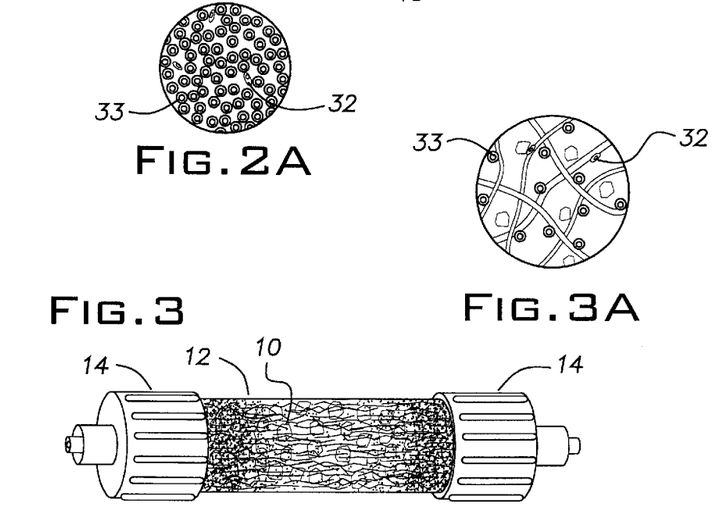
FIG. 2A is an exploded view of bone marrow aspirate showing progenitor cells and marrow-derived nucleated cells.
FIG. 3 is a perspective view of a matrix container containing a graft matrix having a nonuniform distribution of progenitor cells.
FIG. 3A is an exploded view of the center region of a graft matrix that has been flowed through with bone marrow aspirate.
Figure 3B:
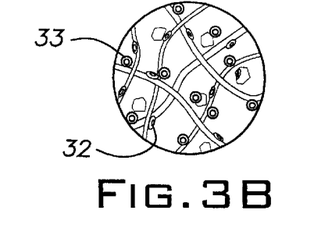
FIG. 3B is an exploded view of an end region of a graft matrix that has been flowed through with bone marrow aspirate.

Following the above procedure, loading syringes 28 and 29 are detached from endcaps 14. As can be seen in FIG. 3, the progenitor cells 32 retained in matrix 10 are distributed nonuniformly within the matrix 10. Specifically, a progenitor cell concentration gradient exists within matrix 10 whereby progenitor cells 32 are concentrated in the regions near the ends of column 12 (see FIG. 3A), where bone marrow aspirate 20 first contacts the matrix material upon entering column 12. Consequently, the central region of matrix 10 has a much lower population of progenitor cells 32 (see FIG. 3B). This effect is due to rapid adherence of progenitor cells and other cells to the matrix surface upon entering column 12. Thus, a mechanical mixing step is effective to produce an enriched matrix having a more uniform progenitor cell distribution.

Figure 4:
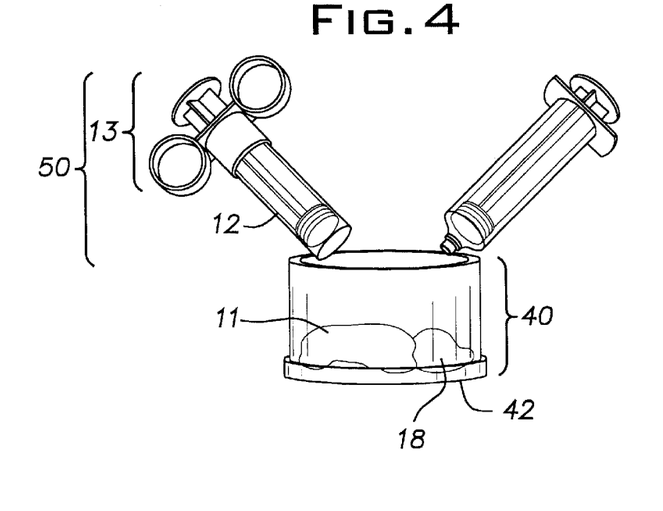
FIG. 4 is a perspective view of a mixing bowl containing clot material and enriched matrix material.

Referring to FIG. 4, the endcaps are removed from column 12, and column 12 is fitted with a syringe adaptor 13 to form an applicator syringe 50. Syringe adaptor 13 comprises a plunger which is adapted to plunge column 12, and expel matrix material therefrom. The progenitor cell-enriched matrix material 11 is thus expelled from column 12, and delivered into mixing bowl 40 together with a volume of clot material 18. Clot material 18 is preferably non-anticoagulated bone marrow aspirate obtained from the graftee that has been allowed to clot as above-described. Optionally the non-anticoagulated bone marrow aspirate can be combined with the enriched matrix prior to clotting, allowing the clot to form during and after the mixing process. The ratio of clot material volume to progenitor cell-enriched matrix material volume is preferably about 1:1, less preferably about or at least 1:5, 1:4, 1:3, 1:2, 2:1, 3:1, 4:1, or 5:1. Once combined in mixing bowl 40, the enriched matrix material 11 and clot material 18 are mechanically mixed together to provide a heterogeneous implantable composite bone graft mixture 8 (see FIG. 5) of substantially uniform composition. By substantially uniform composition, it is meant that the composite bone graft mixture 8 comprises the fibrous and particulate bone material of the composite matrix, an enriched population of progenitor cells, and clot material, all substantially uniformly distributed throughout the entire mixture, thus exhibiting substantially no bulk concentration gradient for any single component. Such mechanical mixing can be performed, for example, with a spatula tool 38 in mixing bowl 40, or via any other known mechanical mixing means.

Figures 5, 6:
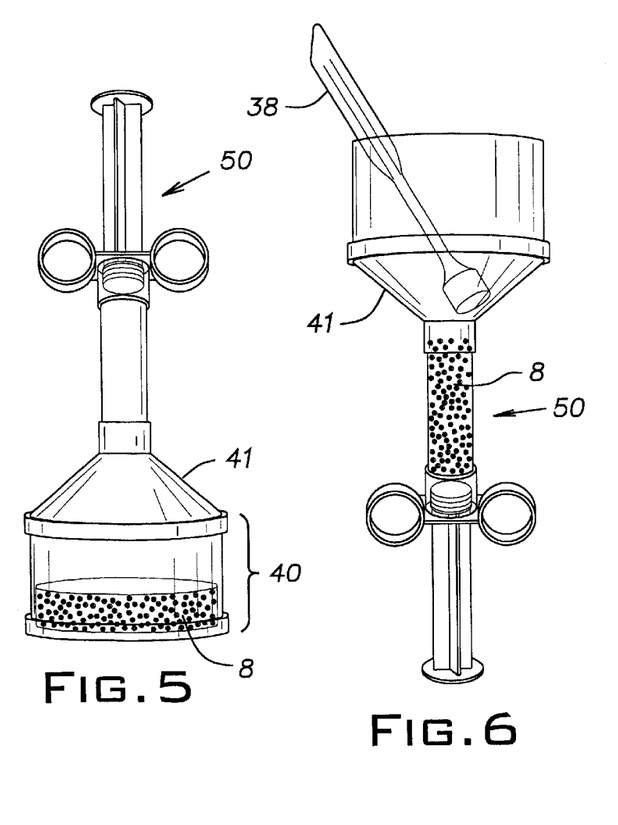
FIG. 5 is a perspective view of an assembly comprising a mixing bowl, funnel and applicator syringe.
FIG. 6 is a perspective view of the assembly of FIG. 5 which has been inverted to carry out a preferred embodiment of the invention.

Referring to FIG. 5, funnel 41 is fitted to mixing bowl 40 (still containing composite bone marrow graft material 8), and applicator syringe 50 is fitted to funnel 41 as shown. The entire apparatus as shown in FIG. 5 is subsequently inverted as shown in FIG. 6, and base cover 42 of mixing bowl 40 is removed. Optionally, the bowl contents may be poured or scooped into the funnel 41 affixed to applicator syringe 50. Implantable composite bone marrow graft material 8 is then packed into applicator syringe 50. Spatula tool 38 can be used to aid packing. Optionally, spatula tool 38 is equipped at one end with a plunger adapted to pack the material into the applicator syringe as shown. Once packed, applicator syringe 50 is removed from funnel 41, and can be used to apply the implantable composite bone marrow graft material 8 to the patient. Graft material 8 is effective to induce bone healing or bone regeneration at the graft site. Optionally, the composite bone marrow graft material may be transferred directly from the mixing bowl to the patient by other mechanical means known in the art.

Figure 7:
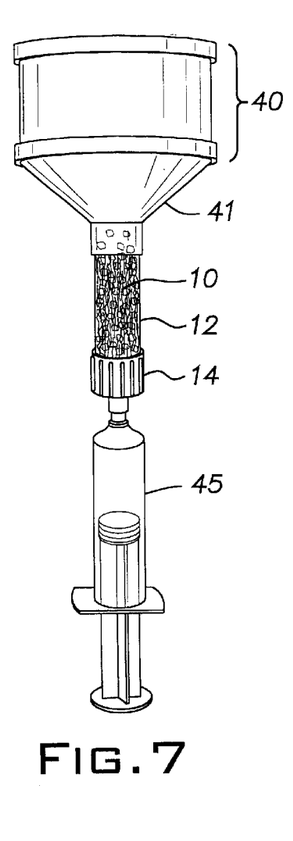
FIG. 7 is a perspective view of an assembly comprising a mixing bowl, funnel, matrix container, and effluent syringe for carrying out a second preferred embodiment of the invention.

Composite bone marrow graft material according to the invention can also be prepared according to a second preferred embodiment as follows. Composite matrix 10 and bone marrow aspirate 20 (preferably containing an anticoagulant) are separately obtained and prepared as above-described, and are separately placed in mixing bowl 40 in similar proportion as described with respect to the first preferred embodiment above. The matrix and aspirate are then mechanically mixed together using spatula tool 38, or some other known mechanical mixing means to provide an enriched matrix. The liquid aspirate 20 is then drained from the enriched matrix 11 as follows. Referring to FIG. 7, funnel 41 is attached to mixing bowl 40, and column 12 is attached to funnel 41 as shown, with a single endcap 14 connected at the opposite end of column 12. Endcap 14 is also fitted with a membrane or screen (not shown) having openings adapted to allow aspirate to pass through while retaining the enriched matrix 11. The openings are preferably at least 20, more preferably 30, more preferably 40, $\mu$m in diameter. An effluent syringe 45 is attached to endcap 14 via known connecting means, thus providing fluid communication between the respective interior volumes of effluent syringe 45 and column 12. The entire apparatus thus described is inverted as shown in FIG. 7, and base cover 42 is removed if necessary. The liquid within mixing bowl 40 is drawn or drained through column 12 and into effluent syringe 45. The liquid may be plunged back through column 12. This back and forth procedure may be repeated several times as described previously. The depleted liquid is then discarded.

Alternatively, liquid aspirate 20 can be drained from the enriched matrix by compressing the enriched matrix between a wall of a container (e.g. the base of mixing bowl 40) and a porous screen or membrane (not shown) with openings adapted to allow aspirate to pass therethrough, but to retain the enriched matrix compressed against the container wall. Liquid aspirate which has permeated the membrane is then decanted, leaving the enriched matrix compressed in the container between the container wall and the porous membrane. Preferably, the container is a syringe which is fitted with a porous membrane upstream of its outlet, and the container wall is a syringe plunger. In this preferred embodiment, compression of the enriched matrix is achieved by plunging the matrix toward the porous membrane within the syringe, thereby expelling aspirate through the outlet while retaining the enriched matrix within the syringe.

Now-enriched matrix 11 is then combined with a volume of clot material 18 as shown in FIG. 4, and the method proceeds similarly as above-described with respect to the first preferred embodiment to produce an implantable composite bone marrow graft material 8 which is effective to induce bone healing or bone regeneration in the graftee.

Optionally, an additional step can be added to each of the preferred embodiments as described above. Prior to implantation of implantable bone graft material 8, a quantity of non-anticoagulated bone marrow aspirate can be delivered (such as via draining) to the graft material 8 prior to clotting, for example while graft material 8 is in applicator syringe 50. In this manner, liquid aspirate will permeate the void volume of graft material 8, ultimately coagulating therein. The aspirate must be delivered to graft material 8 immediately following aspiration to ensure it remains liquid long enough to effectively permeate the material. This step provides additional marrow-derived nucleated cells (including additional progenitor cells) to implantable graft material 8.

The invented method of preparing composite bone marrow graft material typically requires less than sixty minutes to complete. Thus, the invented method can be performed while the bone marrow donor/graftee is in the operating room. Accordingly, the number of occasions the graftee must undergo invasive procedures to receive a composite bone graft can be reduced using the invented method.

Figure 8:
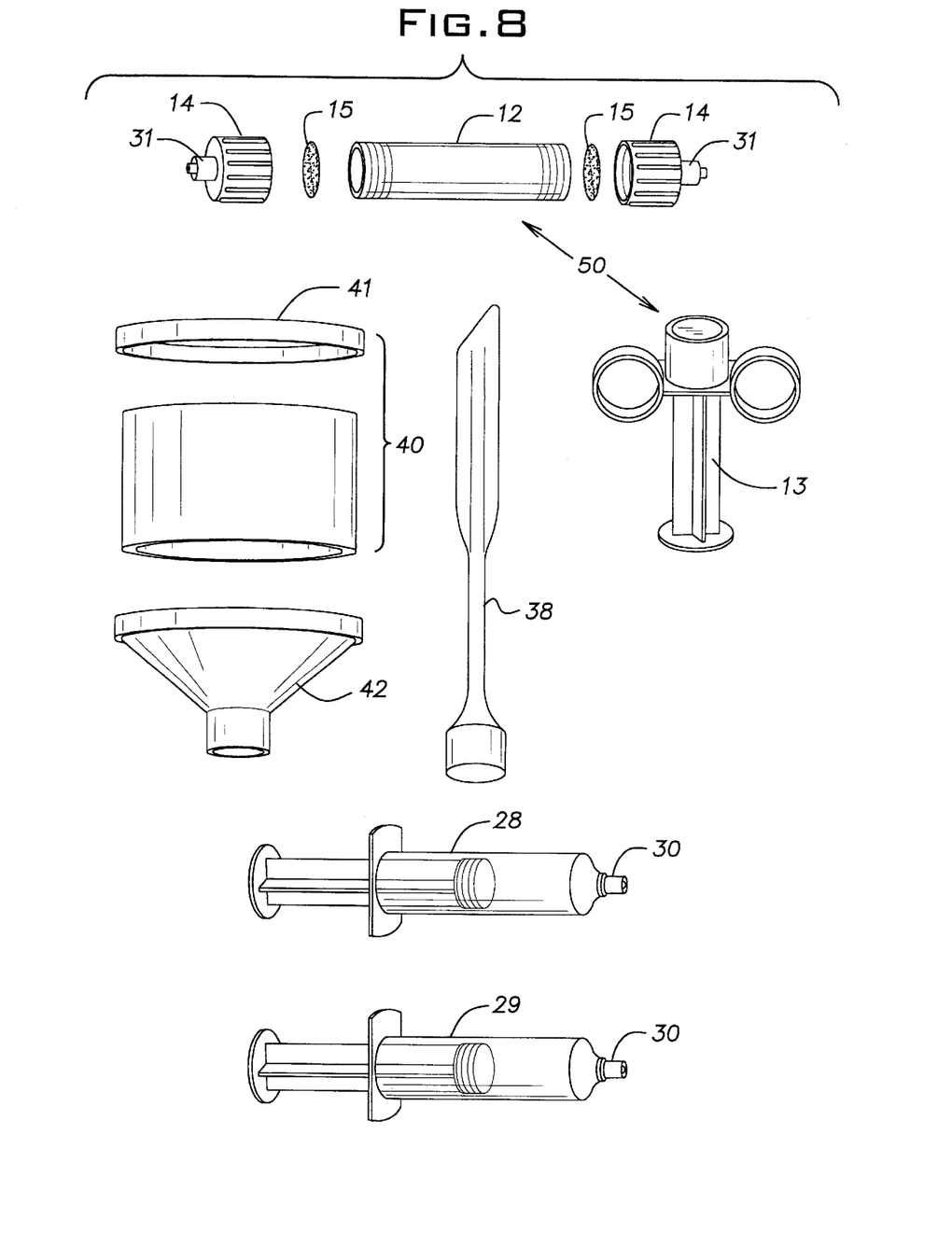
FIG. 8 is a perspective view of a kit according to the present invention.

A kit according to the invention is also provided to assist surgeons in performing the invented method. Referring to FIG. 8, such a kit would preferably enable performance of the method according to either of the preferred embodiments described above, and preferably comprises at least the following sterilized implements, preferably made of plastic, preferably transparent or translucent: a matrix container (e.g. matrix column 12), at least one endcap 14 releasably attachable to the matrix container via known attachment means, endcap connector 31 on endcap 14 for fluid connection with loading syringes, at least one loading syringe 28 having a syringe connector 30 for fluid connection with endcap 14, a mixing bowl 40 with removable base cover 42, a funnel 41 adapted at one end to mate with an open end of mixing bowl 40 and at the other end to mate with column 12, a syringe adaptor 13 for converting column 12 into an applicator syringe, and a spatula tool 38. Most preferably, the kit further comprises a second loading syringe 29 and a second endcap 14, similarly constituted as described above. Optionally, the kit is provided with a porous biocompatible implanted substrate for use as a bone graft matrix, and porous membranes 15 to retain a matrix within the matrix container. Optionally, the invented kit can additionally comprise heparinized bone marrow aspiration syringes, aspiration needles, additional loading syringes, or other implements useful in the bone grafting art.

The following Example further illustrates various aspects of the invention.

EXAMPLE 1

It has already been shown that bone graft material having an enriched matrix exhibits improved performance over non-enriched grafts (See U.S. Pat. Nos. 5,824,084 and 6,049,026). The following experiment demonstrated the further efficacy of graft material that combined an enriched matrix with an aspirated bone marrow clot (ABMC).

Posterior spinal fusion was performed in 22 beagle dogs. Localized fusions were performed at three separate spinal fusion sites in each animal (L1–2, L3–4, and L5–6). Three types of composite bone grafts were prepared using cancellous bone chips as the matrix material. In 11 of the dogs, demineralized cancellous bone chips were used, while mineralized cancellous bone chips were used in the remaining 11 dogs. The three composite grafts were enriched matrix alone, non-enriched matrix including a bone marrow clot, and enriched matrix including a bone marrow clot. Enrichment is achieved as described above by combining the matrix material with an excess volume of aspirate.

Fusions were compared using union score as the primary outcome parameter. Bone volume at each site was also assessed using quantitative analysis of CT scans and mechanical testing was performed at each site. Tables 1 and 2 summarize the union score for each composite in each animal and graft site for mineralized and demineralized matrix respectively.

TABLE 1

Union score for each composite by animal and graft site for mineralized cancellous bone matrix cubes

| | Enriched Alone | | | ABMC Alone | | | Enriched + ABMC | | |
|---|---|---|---|---|---|---|---|---|---|
| Animal | L1-2 | L3-4 | L5-6 | L1-2 | L3-4 | L5-6 | L1-2 | L3-4 | L5-6 |
| 1 | | | 0 | | 1.5 | | | 2.0 | |
| 2 | 0 | | | | 0 | | | | 0.5 |
| 3 | | | 4.0 | 4.0 | | | | 4.0 | |
| 4 | | 1.0 | | | | 3.5 | 2.0 | | |
| 5 | | 0 | | 1.0 | | | | | 4.0 |
| 6 | 0 | | | | | 0.5 | | 3.0 | |
| 7 | | 0 | | | | 0 | 0 | | |
| 8 | | 1.0 | | | 2.5 | | | 1.5 | |
| 9 | | | 0 | 0 | | | | | 0 |
| 10 | 0 | | | | | 0.5 | | 1.0 | |
| 11 | | 1.0 | | | 0 | | | | 3.0 |
| SUB-TOTAL | 0 | 2.0 | 5.0 | 5.0 | 4.0 | 4.5 | 5.5 | 8.0 | 7.5 |
| TOTAL | | 7.0 | | | 13.5 | | | 21.0 | |
| Mean | | 0.6 | | | 1.2 | | | 1.9 | |
| Median | | 0 | | | 0.5 | | | 2.0 | |

TABLE 2

Union score for each composite by animal and graft site for demineralized cancellous bone matrix cubes

| | Enriched Alone | | | ABMC Alone | | | Enriched + ABMC | | |
|---|---|---|---|---|---|---|---|---|---|
| Animal | L1-2 | L3-4 | L5-6 | L1-2 | L3-4 | L5-6 | L1-2 | L3-4 | L5-6 |
| 1 | | 3.0 | | | | | | 4.0 | 4.0 |
| 2 | | | 0 | | 4.0 | | | | 0.5 |
| 3 | 0 | | | | | 1.5 | | 4.0 | |
| 4 | 0 | | | | 3.0 | | | | 1.0 |
| 5 | | 3.0 | | 1.0 | | | | | 4.0 |
| 6 | | | 1.5 | 2.5 | | | | 4.0 | |
| 7 | | | 1.0 | 0 | | | | 0 | |
| 8 | 0 | | | | 0 | | | | 0 |
| 9 | | 0 | | | | 0 | 0 | | |
| 10 | | | 0 | 0 | | 0 | | | |
| 11 | 0.5 | | | | 0 | | | | 3.0 |
| SUB-TOTAL | 0.5 | 6.0 | 2.5 | 3.5 | 7.0 | 5.5 | 4.5 | 8.0 | 8.0 |
| TOTAL | | 9.0 | | | 16.0 | | | 20.5 | |
| Mean | | 0.8 | | | 1.5 | | | 1.9 | |
| Median | | 0 | | | 1.0 | | | 1.0 | |

The above data indicate that addition of bone marrow clot material to a bone graft matrix significantly enhances the efficacy of the composite graft. When mineralized cancellous bone matrix was used, the union score was greatest for the Enriched+ABMC group (mean=1.9). Furthermore, the union scores of the Enriched+ABMC group were significantly greater than those for Enriched Alone (mean=0.6, p=0.008). The Enriched+ABMC group was also statistically superior to the ABMC Alone group (mean 1.2, p=0.04). This degree of superior performance was surprising and unexpected. The overall union rates for the three composites, Enriched+ABMC, ABMC Alone, and Enriched Alone were 9 of 11 (81%), 7 of 11 (63%) and 4 of 11 (36%) respectively. Fusion sites with higher fusion scores were clustered in the Enriched+ABMC group. In the Enriched+ABMC group, 4 of 11 fusion sites (36%) were graded 3.0 or higher. In contrast, only 1 of 11 (8.3%) sites in the Enriched Alone group and 2 of 11 sites (18%) in the ABMC Alone group were similarly graded.

When demineralized cancellous bone matrix was used, the union score was also greatest for the Enriched+ABMC group. The overall union rates for the three materials, Enriched+ABMC, ABMC Alone, and Enriched Alone were 7 of 11 (63%), 6 of 11 (54%) and 5 of 11 (45%) respectively. Again, fusion sites with higher fusion scores were clustered in the Enriched +ABMC group. In the Enriched+ABMC group, 5 of 11 fusion sites (45%) were graded 3.0 or higher. In contrast, only 2 of 11 fusion sites (18%) in the Enriched Alone group and 3 of 11 (27%) fusion sites in the ABMC Only group were graded at this level. The combination of ABMC with enriched bone matrix provided a bone graft exhibiting surprisingly and unexpectedly superior performance compared to an enriched bone matrix.

Mechanical testing was also conducted for all specimens. Data for maximum load, deformation to failure and energy to failure were calculated only for those specimens in which a bony union provided a defined yield point. Mechanical test data is summarized below in tables 3 and 4 for demineralized and mineralized samples respectively.

Stiffness was measured for each graft site, and the data tabulated to yield mean and standard deviation values for each of the three graft types for both mineralized and demineralized bone matrices. For mineralized bone matrix, the Enriched Alone, ABMC Alone and Enriched+ABMC grafts exhibited stiffness of 6.9±2.4, 7.9±2.3, and 8.2±4.2, respectively. For demineralized bone matrix, the Enriched Alone, ABMC Alone and Enriched+ABMC grafts exhibited stiffness of 9.1±6.0, 9.4±6.2, and 9.6±4.8, respectively.

CT image analysis data was obtained for each composite graft regarding fusion volume, fusion area and mean bone density within the fusion mass. The data is summarized for mineralized and demineralized cancellous bone matrix in tables 3 and 4 respectively. As is evident from tables 3 and 4, both fusion volume and fusion area were greatest for the Enriched+ABMC group.

TABLE 3

CT data for each cell-matrix composite using mineralized cancellous bone matrix

| | Enriched Alone (n = 11) | ABMC Alone (n = 11) | Enriched + ABMC (n = 11) |
|---|---|---|---|
| Fusion Volume ($mm^3$) | 869 ± 196 | 961 ± 115 | 1006 ± 185 |
| Fusion Area ($mm^2$) | 81 ± 17 | 91 ± 14 | 95 ± 27 |
| Bone Density | 1848 ± 62 | 1840 ± 43 | 1824 ± 66 |

TABLE 4

CT data for each cell-matrix composite using demineralized cancellous bone matrix

|  | Enriched Alone (n = 11) | ABMC Alone (n = 11) | Enriched + ABMC (n = 11) |
|---|---|---|---|
| Fusion Volume (mm$^3$) | 872 ± 288 | 1010 ± 268 | 1115 ± 406 |
| Fusion Area (mm$^2$) | 85 ± 31 | 95 ± 27 | 98 ± 31 |
| Bone Density | 1901 ± 35 | 1858 ± 29 | 1854 ± 77 |

Although the hereinabove described embodiments of the invention constitute the preferred embodiments, it should be understood that modifications can be made thereto without departing from the scope of the invention as set forth in the appended claims.

What is claimed is:

1. A composite bone marrow graft material comprising a porous biocompatible implantable matrix and clot material, said composite bone marrow graft material having an enriched population of progenitor cells, said clot material comprising a material selected from the group consisting of a blood clot, a bone marrow clot, platelet gel, platelet concentrate, fibrin clot material and fibrin glue.

2. A composite bone marrow graft material according to claim 1, said progenitor cells comprising connective tissue progenitor cells.

3. A composite bone marrow graft material according to claim 1, said progenitor cells comprising stem cells.

4. A composite bone marrow graft material according to claim 3, said stem cells comprising pleuripotent stem cells.

5. A composite bone marrow graft material according to claim 1, wherein said implantable matrix comprises particulate bone material and fibrous bone material.

6. A composite bone marrow graft material according to claim 5, wherein said particulate bone material comprises allograft cancellous bone particles.

7. A composite bone marrow graft material according to claim 5, wherein said fibrous bone material comprises allograft demineralized cortical bone fibers.

8. A composite bone marrow graft material according to claim 1, wherein said matrix comprises a matrix material selected from the group consisting of ceramic material, bioglass, collagen, mineralized bone, demineralized bone, hyaluronic acid, and synthetic biopolymer material.

9. A composite bone marrow graft material according to claim 1, wherein said clot material is a bone marrow clot derived from bone marrow aspirate.

10. A composite bone marrow graft material according to claim 1, wherein said clot material is a blood clot.

11. A composite bone marrow graft material according to claim 1, wherein said clot material is a material selected from the group consisting of platelet gel, platelet concentrate, fibrin clot material, and fibrin glue.

12. A composite bone marrow graft material according to claim 1, wherein the ratio of progenitor cells to all marrow-derived nucleated cells is at least 1:20,000.

13. A composite bone marrow graft material according to claim 1, said implantable matrix and said clot material being present in said graft material in a volume ratio of 5:1 to 1:5.

14. A composite bone marrow graft material according to claim 1, said progenitor cells, said clot material, and said matrix all being substantially uniformly distributed throughout said composite bone marrow graft material.

15. A composite bone marrow graft material according to claim 1, wherein cell adhesion molecules are bound to the surface of said implantable matrix.

16. A composite bone marrow graft material according to claim 1, said graft material being effective to induce bone healing in a graftee.

17. A composite bone marrow graft material according to claim 1, said graft material being effective to induce bone regeneration in a graftee.

18. A method of preparing composite bone marrow graft material comprising the steps of:
 a) providing a bone marrow aspirate;
 b) providing a porous biocompatible implantable matrix;
 c) contacting said bone marrow aspirate and said matrix to provide an enriched matrix;
 d) adding clot material to said enriched matrix, said clot material comprising a material selected from the group consisting of a blood clot, a bone marrow clot, platelet gel, platelet concentrate, fibrin clot material and fibrin glue; and
 e) mechanically mixing said enriched matrix and said clot material to yield a composite bone marrow graft material having progenitor cells distributed substantially uniformly throughout said composite bone marrow graft material.

19. A method according to claim 18, wherein said implantable matrix comprises particulate bone material and fibrous bone material.

20. A method according to claim 19 wherein said particulate bone material comprises allograft cancellous bone particles, and said fibrous bone material comprises demineralized cortical bone fibers.

21. A method according to claim 20, wherein said implantable matrix comprises about 1–25 cc bulk volume of particulate bone particles and about 25–1000 mg dry weight of bone fibers.

22. A method according to claim 20, said bone fibers having lengths of 5 mm-15 cm.

23. A method according to claim 18, further comprising the step of adding non-anticoagulated bone marrow aspirate to said enriched matrix.

24. A kit for the preparation of composite bone marrow graft material, said kit comprising a matrix container, a first endcap, a second endcap, a first loading syringe, and a second loading syringe, said first endcap being releasably attachable to said matrix container, said first endcap and said first loading syringe being adapted to connect to each other to provide fluid communication between said first loading syringe and said matrix container, said second endcap being releasably attachable to said matrix container, said second endcap and said second loading syringe being adapted to connect to each other to provide fluid communication between said second loading syringe and said matrix container.

25. A kit according to claim 24, said kit further comprising a porous biocompatible implantable matrix.

26. A kit according to claim 24, said kit further comprising heparinized aspiration syringes and aspiration needles.

27. A kit according to claim 24, said kit further comprising a syringe adaptor adapted to mate with said matrix container to form an applicator syringe therewith.

28. A kit according to claim 27, said kit further comprising a mixing bowl with a removable base cover and a funnel, said funnel adapted to mate with an open end of said mixing bowl at one end thereof, and with said applicator syringe at a second end thereof.

29. A kit according to claim 24, said kit further comprising a spatula tool, said spatula tool having a plunger at an end thereof, said plunger adapted to pack graft material into said matrix container.

30. A kit according to claim 24, said kit further comprising a porous membrane effective to retain matrix material within said container.

31. A kit according to claim 24, wherein said matrix container is a matrix column.

32. A kit for the preparation of composite bone marrow graft material, said kit comprising a matrix container, a first endcap, a first loading syringe, and a spatula tool, said first endcap being releasably attachable to said matrix container, said first endcap and said first loading syringe being adapted to connect to each other to provide fluid communication between said first loading syringe and said matrix container, said spatula tool basing a plunger at an end thereof, said plunger being adapted to pack graft material into said matrix container.

33. A kit according to claim 32, further comprising a porous biocompatible implantable matrix.

34. A kit according to claim 32, further comprising a heparinized aspiration syringe and an aspiration needle.

35. A kit according to claim 32, further comprising a porous membrane effective to retain matrix material within said container.

36. A kit according to claim 32, further comprising a mixing bowl having a removable base cover and a funnel, said funnel being adapted to mate with an open end of said mixing bowl at a first end thereof, and with said applicator syringe at a second end thereof.

* * * * *